United States Patent
Knies et al.

(10) Patent No.: US 8,487,124 B2
(45) Date of Patent: Jul. 16, 2013

(54) CYCLIC AZA-SILA COMPOUNDS

(75) Inventors: Wolfgang Knies, Burghausen (DE); Hans Eiblmeier, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/147,869

(22) PCT Filed: Feb. 12, 2010

(86) PCT No.: PCT/EP2010/051799
§ 371 (c)(1),
(2), (4) Date: Aug. 4, 2011

(87) PCT Pub. No.: WO2010/097303
PCT Pub. Date: Sep. 2, 2010

(65) Prior Publication Data
US 2011/0301373 A1     Dec. 8, 2011

(30) Foreign Application Priority Data
Feb. 26, 2009    (DE) .......................... 10 2009 001 181

(51) Int. Cl.
*C07F 7/10*    (2006.01)
(52) U.S. Cl.
USPC .......................................... 556/410; 556/409
(58) Field of Classification Search
USPC .............................. 556/409, 422, 410; 528/28
See application file for complete search history.

(56) References Cited

U.S. PATENT DOCUMENTS
3,565,934 A     2/1971    Fink
6,329,487 B1 *  12/2001   Abel et al. ...................... 528/21

FOREIGN PATENT DOCUMENTS
WO    2004044958 A2    5/2004

OTHER PUBLICATIONS

Shimizu et al, Journal of organometallic Chemistry, 611, (2000), 12-19.*
Grey et al, Journal of American Chemical Society, 1987, 109, 6577-6585.*
Gusel'nikov, Coordination Chemistry Reviews, 244 (2003) 149-240.*
Soldner et al, Inorganic Chemistry 1998, 37, 510-515.*
Andersch et al., "Structure of 1,3,5-Trimethyl-2,2,4,4,6,6-hexakis(methylamino)cyclotrisilazane", Acta Cryst., vol. C46, pp. 1180-1181 (1990).
International Search Report for PCT/EP2010/051799 dated Apr. 7, 2010.
Veith et al., "Polycyclische Silylamide von Ge11 and Sn11 mit unterschiedlichen Strukturen—Bis(germandiyl) versus Distannat", Angew. Chem, vol. 100, pp. 1124-1125 (1988).

* cited by examiner

*Primary Examiner* — Johann R Richter
*Assistant Examiner* — Pancham Bakshi
(74) *Attorney, Agent, or Firm* — Caesar, Rivise, Bernstein, Cohen & Pokotilow, Ltd.

(57) ABSTRACT

The invention relates to cyclic aza-sila compounds that are made of 4 to 10 units of the general formulas (I) and (II) bonded by means of Si—Si or Si—N single bonds, wherein Y is selected from among —NR$^1$R$^2$, hydrogen, and a halogen, R$^1$ and R$^2$ are selected from among hydrogen and a hydrocarbon group having 1 to 20 carbon atoms, and R$^3$ is a hydrocarbon group having 1 to 20 carbon atoms, with the stipulation that at least two units of the general formula (I) are bonded to each other in the ring by means of an Si—Si single bond, that at most 35 mol % of the groups Y is a hydrogen, and that at most 15 mol % of the groups Y is a halogen, and to a method for the production thereof.

15 Claims, No Drawings

CYCLIC AZA-SILA COMPOUNDS

BACKGROUND OF THE INVENTION

The invention relates to cyclic aza-sila compounds formed from 4 to 10 units bonded via Si—Si or Si—N single bonds, and to the preparation thereof.

Aminosilane compounds are of great interest for the production of Si—N and Si—O layers. Amino-substituted monosilanes have already been studied for this purpose; some disilanes also exhibit good properties. In this respect, there is an interest in compounds with a high silicon content. Of particular interest are the cycles, which are yet to be described, having a high silicon content due to adjacent silicon atoms.

U.S. Pat. No. 3,565,934 describes the thermolysis of aminosilanes, in which 1,3-diazadisilacyclobutanes are formed. This reaction is promoted by amine chloride radicals. Ammonium salts lead to an elimination of amine from the aminosilane.

WO 2004/044958 describes the preparation of a 1,3-diazadisilacyclobutane from an aminochlorosilane with tert-butyllithium.

SUMMARY OF THE INVENTION

The invention provides cyclic aza-sila compounds formed from 4 to 10 units which are bonded via Si—Si or Si—N single bonds and are of the general formulae (I) and (II)

$$=SiY_2 \qquad (I)$$

$$=NR^3 \qquad (II)$$

where
Y is selected from —NR$^1$R$^2$, hydrogen and halogen,
R$^1$ and R$^2$ are selected from hydrogen and hydrocarbyl radical having 1 to 20 carbon atoms and
R$^3$ is a hydrocarbyl radical having 1 to 20 carbon atoms, with the proviso that at least two units of the general formula (I) in the ring are bonded to one another via an Si—Si single bond, that at most 35 mol % of the Y radicals are hydrogen and at most 15 mol % of the Y radicals are halogen.

The cyclic aza-sila compounds are evaporable and therefore outstandingly suitable for the production of Si—N and Si—O layers.

R$^1$, R$^2$ and R$^3$ are preferably linear or branched alkyl, cycloalkyl, aryl, alkenyl or arylalkyl radicals, preferably alkyl radicals. The R$^1$, R$^2$ and R$^3$ radicals preferably have 1 to 12, especially 1 to 6, carbon atoms. Particularly preferred R$^1$, R$^2$ and R$^3$ radicals are methyl, ethyl, n-propyl, isopropyl, n-butyl, isobutyl, tert-butyl, n-pentyl, isopentyl, neopentyl or tert-pentyl radical and phenyl radical.

In the general formula (I), preferably at most 20 mol %, more preferably at most 10 mol %, especially none, of the Y radicals is hydrogen. When Y is halogen, preference is given to bromine and iodine and especially chlorine.

In the general formula (I), preferably at most 1 mol %, more preferably at most 0.1 mol %, especially at most 0.01 mol %, especially preferably none, of the Y radicals is halogen.

Preferably, Y is the —NHR$^2$ radical. R$^2$ is preferably as defined for R$^3$.

The cyclic aza-sila compounds are preferably formed from 4, 6 or 10 units of the general formulae (I) and (II). Particular preference is given to cyclic aza-sila compounds formed from 3 or 4 units of the general formula (I) and 1 or 2 units of the general formula (II).

Particularly preferred cyclic aza-sila compounds are the 1-aza-2,3,4-trisilacyclobutanes, especially the 1-alkyl-2,2,3,3,4,4-hexakisalkylamino-1-aza-2,3,4-trisilacyclobutanes and the 1,4-diaza-2,3,5,6-tetrasilacyclohexanes, especially the 1,4-dialkyl-2,2,3,3,5,5,6,6-octakisalkylamino-1,4-diaza-2,3,5,6-tetrasilacyclohexanes.

The cyclic aza-sila compounds can be prepared by reacting linear oligosilanes of the general formula (III)

$$Y(SiY_2)_mSiY_3 \qquad (III)$$

with amine salts of the general formula (IV)

$$X(H_2NR^3) \qquad (IV)$$

where
X is a halogen atom and
m has the values of 1, 2 or 3 and
R$^3$ and Y are each as defined above.

To control the ring size, the ratios used for the oligosilanes of the general formula (III) and the amine salts of the general formula (IV) are selected.

Preferably, X is a chlorine atom.

Preferably, amine salt of the general formula (IV) is used in deficiency with respect to the linear oligosilane of the general formula (III).

Preferably, in the reaction, at least 0.1% by weight, more preferably at least 1% by weight, of amine salt of the general formula (IV) is present, based on the linear oligosilanes of the general formula (III).

The conversion temperature is preferably at least 20° C., more preferably at least 50° C., and preferably at most 200° C., more preferably at most 150° C. The upper temperature limit is preferably guided by the boiling point of the compounds used.

The process can be performed in a solvent, especially nonpolar solvent. Preference is given to hydrocarbons and halogenated hydrocarbons. Solvent mixtures having a boiling point or boiling range of up to 150° C. at 1 bar are preferred. Examples of such solvents are the alkanes having 3 to 10 carbon atoms, aromatics having 6 to 12 carbon atoms, halogenated alkanes having 1 to 3 carbon atoms, and mixtures thereof. Preferred examples are dichloromethane, tetrachloromethane, butane, pentane, hexane, heptane, octane, benzene, toluene and xylenes, and the isomer mixtures thereof.

The progress of the reaction can be monitored by the formation of free amine.

The cyclic aza-sila compounds can also be prepared by heating linear oligosilanes of the general formula (III)

$$Y(SiY_2)_mSiY_3 \qquad (III)$$

where
m has the values of 1, 2 or 3, and
Y is as defined above.

The linear oligosilanes of the general formula (III) can disproportionate in this preparation process.

The conversion temperature is preferably at least 80° C., more preferably at least 120° C., and preferably at most 250° C., more preferably at most 200° C. The upper temperature limit is preferably guided by the boiling point of the compounds used.

The reaction preferably takes place in the presence of Lewis bases. Examples of bases are hydroxides such as alkali metal and alkaline earth metal hydroxides, especially LiOH, NaOH, KOH, RbOH, CsOH, Mg(OH)$_2$, Ca(OH)$_2$, Sr(OH)$_2$, Ba(OH)$_2$, ammonia, amines, amides such as sodium and potassium amide, silazides such as lithium silazide, hydrides such as sodium, potassium and calcium hydride, alkoxides such as isopropoxide, ethoxide and methoxide. Preferred bases are amines, especially primary and secondary amines, and silazides such as lithium silazide.

Preferably, in the reaction, at least 0.1% by weight, more preferably at least 1% by weight, of base is present, based on the linear oligosilanes of the general formula (III).

In a particular embodiment, the amines formed in the reaction act as a catalyst. The amines are preferably hindered from escaping from the reaction mixture. This is preferably accomplished by increasing the pressure.

The process can be performed in a solvent, especially nonpolar solvent. Preference is given to the aforementioned solvents, though high-boiling solvents are also preferred.

DETAILED DESCRIPTION OF PREFERRED EMBODIMENTS

All above symbols in the above formulae are each defined independently of one another.

In the examples which follow, unless stated otherwise in each case, all amounts and percentages are based on weight, all pressures are 1 bar (abs.) and all temperatures are 20° C.

Example 1

Preparation of 1,4-diethyl-2,2,3,3,5,5,6,6-octakis-ethylamino-1,4-diaza-2,3,5,6-tetrasilacyclohexane 38 g of hexakisethylaminodisilane with a purity of 98% were admixed with 1.3% by weight of ethylamine hydrochloride and heated at reflux for 7 hours. The temperature rose briefly to 135° C. and fell after a few minutes to 115° C. This formed 9 g of 1,4-diethyl-2,2,3,3,5,5,6,6-octakisethylamino-1,4-diaza-2,3,5,6-tetrasilacyclohexane.

When 7% by weight of ethylamine hydrochloride was used, 40 g of hexakisethylaminodisilane formed, under the same reaction conditions, 18 g of 1,4-diethyl-2,2,3,3,5,5,6,6-octakisethylamino-1,4-diaza-2,3,5,6-tetrasilacyclohexane.

Example 2

Preparation of 1-ethyl-2,2,3,3,4,4-hexakisethylamino-1-aza-2,3,4-trisilacyclobutane Heating of 40 g of hexakisethylaminodisilane in a glass flask with a reflux condenser at 150° C. under flowing nitrogen formed, after 35 h, a mixture of 25 g of tetrakisethylaminosilane and 2 g of 1-ethyl-2,2,3,3,4,4-hexakisethylamino-1-aza-2,3,4-trisilacyclobutane. 1,4-diethyl-2,2,3,3,5,5,6,6-octakisethylamino-1,4-diaza-2,3,5,6-tetrasilacyclohexane was detectable only in traces. In contrast to example 1, the temperature remained constant at 150° C.

Example 3

Preparation of 1-ethyl-2,2,3,3,4,4-hexakisethylamino-1-aza-2,3,4-trisilacyclobutane 4 g of hexakisethylaminodisilane were introduced into a steel tube which had pressure-tight screw closures at both ends. The tube was heated to 150° C. for 5 days. In addition to undecomposed starting material, 4% by weight of octakisethylaminotrisilane and 11% by weight of 1-ethyl-2,2,3,3,4,4-hexakisethylamino-1-aza-2,3,4-trisilacyclobutane were found. The sample contained 9% by weight of ethylamine, which, in contrast to examples 1 and 2, could not escape.

The invention claimed is:

1. A cyclic aza-sila compound represented by the following structure:

where n is 4 to 10 and each Z is independently selected from general formulae (I) and (II)

$$=SiY_2 \quad (I)$$

$$=NR^3 \quad (II)$$

where
Y is selected from —$NR^1R^2$, hydrogen and halogen,
$R^1$ and $R^2$ are selected from hydrogen and hydrocarbyl radical having 1 to 20 carbon atoms and
$R^3$ is a hydrocarbyl radical having 1 to 20 carbon atoms,
wherein: (a) each Z is bonded to each adjacent Z via Si—Si or Si—N single bonds, (b) at least two Z units of the general formula (I) in a ring of the compound are bonded to one another via an Si—Si single bond, (c) at most 35 mol % of Y radicals are hydrogen, and (d) at most 15 mol % of the Y radicals are halogen.

2. A cyclic aza-sila compound as claimed in claim 1, in which $R^1$, $R^2$ and $R^3$ are each alkyl radicals.

3. A cyclic aza-sila compound as claimed in claim 1, in which Y is an —$NHR^2$ radical.

4. A cyclic aza-sila compound as claimed in claim 1, which is selected from 1-aza-2,3,4-trisilacyclobutanes and 1,4-diaza-2,3,5,6-tetrasilacyclohexanes.

5. A process for preparing the cyclic aza-sila compound of claim 1, said process comprising:
reacting linear oligosilanes of the general formula (III)

$$Y(SiY_2)_m SiY_3 \quad (III)$$

with amine salts of the general formula (IV)

$$X(H_2NR^3) \quad (IV)$$

where
X is a halogen atom and
m has values of 1, 2 or 3 and
$R^3$ and Y are each as defined above.

6. The process as claimed in claim 5, in which X is a chlorine atom.

7. A process for preparing the cyclic aza-sila compound of claim 1, said process comprising:
heating linear oligosilanes of the general formula (III)

$$Y(SiY_2)_m SiY_3 \quad (III)$$

where
m has the values of 1, 2 or 3, and
Y is as defined above.

8. The process as claimed in claim 7, in which a conversion temperature is at least 80° C.

9. The process as claimed in claim 7, in which the reaction takes place in a presence of a base.

10. The process as claimed in claim 9, in which the base is an amine.

11. The process as claimed in claim 5, in which solvents are used.

12. The process as claimed in claim 8, in which the reaction takes place in a presence of a base.

13. The process as claimed in claim 12, in which the base is an amine.

14. A cyclic aza-sila compound as claimed in claim 2, in which Y is an —$NHR^2$ radical.

15. A cyclic aza-sila compound as claimed in claim 14, which is selected from 1-aza-2,3,4-trisilacyclobutanes and 1,4-diaza-2,3,5,6-tetrasilacyclohexanes.

* * * * *